US006669646B1

(12) United States Patent
Narimatsu et al.

(10) Patent No.: US 6,669,646 B1
(45) Date of Patent: Dec. 30, 2003

(54) ARTERIOSCLEROSIS EVALUATING APPARATUS (75) Inventors: Kiyoyuki Narimatsu, Komaki (JP); Toshihiko Ogura, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 10/407,195

(22) Filed: Apr. 7, 2003

(30) Foreign Application Priority Data

Sep. 19, 2002 (JP) ........................................ 2002-273912

(51) Int. Cl.[7] ................................................. A61B 5/00
(52) U.S. Cl. ........................ 600/485; 600/490; 600/492; 600/494
(58) Field of Search ................................. 600/485, 490, 600/492–496, 500

(56) References Cited

U.S. PATENT DOCUMENTS

| | | | | |
|---|---|---|---|---|
| 5,048,533 A | * | 9/1991 | Muz | 600/492 |
| 5,050,613 A | * | 9/1991 | Newman et al. | 600/483 |
| 5,152,296 A | * | 10/1992 | Simons | 600/483 |
| 5,289,823 A | * | 3/1994 | Eckerle | 600/492 |
| 5,724,980 A | * | 3/1998 | Nakamura et al. | 600/492 |
| 5,743,856 A | | 4/1998 | Oka et al. | |
| 5,743,857 A | * | 4/1998 | Shinoda et al. | 600/496 |
| 6,254,257 B1 | * | 7/2001 | Sieczkowski | 362/365 |
| 6,355,000 B1 | | 3/2002 | Ogura | |

FOREIGN PATENT DOCUMENTS

| | | | | |
|---|---|---|---|---|
| JP | 5-176900 | * | 7/1993 | ................. 600/492 |
| JP | A 8-257002 | | 10/1996 | |
| JP | B2 3140007 | | 12/2000 | |

* cited by examiner

*Primary Examiner*—Robert L. Nasser
(74) *Attorney, Agent, or Firm*—Oliff & Berridge, PLC (57) ABSTRACT

An arteriosclerosis evaluating apparatus including a left-superior-limb-blood-pressure measuring device including a cuff, a right-superior-limb-blood-pressure measuring device including a cuff, a ratio determining means for determining a ratio between a left-superior-limb blood pressure measured by the left-superior-limb-blood-pressure measuring device and a right-superior-limb blood pressure measured by the right-superior-limb-blood-pressure measuring device, an information obtaining device which obtains information that is related to a velocity at which a pulse wave propagates in a first body portion of the subject that includes at least a portion of the left superior limb or a second body portion of the subject that includes at least a portion of the right superior limb, and a display device which displays the left-and-right-superior-limb blood-pressure ratio determined by the left-and-right-superior-limb-blood-pressure-ratio determining device, and the pulse-wave-propagation-velocity-related information obtained by the pulse-wave-propagation-velocity-related-information obtaining device, such that the left-and-right-superior-limb blood-pressure ratio and the pulse-wave-propagation-velocity-related information are comparable with each other by a medical person.

8 Claims, 4 Drawing Sheets

ARTERIOSCLEROSIS EVALUATING APPARATUS

BACKGROUND OF THE INVENTION

1. Field of the Invention

The present invention relates to an arteriosclerosis evaluating apparatus for evaluating absence or presence, or degree, of arteriosclerosis of a superior-limb artery of a living subject. In the present application, the superior-limb artery is defined as encompassing a subclavian artery.

2. Related Art Statement

Atherosclerosis is a sort of arteriosclerosis and is characterized in that lipid, in particular, cholesterol deposits on the inner wall of artery and accordingly the arterial wall thickens. An artery suffering atherosclerosis has stenosis and its diameter reduces. Thus, atherosclerosis is also called arteriostenosis or arteriosclerosis obliterans. Calcification is another sort of arteriosclerosis and is characterized in that the media of artery hardens.

As a sort of device for inspecting arteriosclerosis, in particular, arteriostenosis, there is known an ankle-and-brachium-blood-pressure-index measuring device that inspects the stenosis by utilizing a fact that blood pressure lowers on a downstream side of a stenotic portion of an artery. Japanese Patent No. 3140007 or its corresponding U.S. Pat. No. 6,355,000 discloses an example of the index measuring device. The disclosed device includes two cuffs that are adapted to be worn on an ankle and a brachium of a living subject so as to measure an ankle blood pressure and a brachial blood pressure of the subject, respectively, then calculates an ankle-and-brachium blood-pressure index as a ratio between the ankle blood pressure and the brachial blood pressure, and finally evaluates presence or absence of arteriostenosis based on the thus calculated ankle-and-brachium blood-pressure index.

Generally, an ankle-and-brachium blood-pressure index is calculated as a proportion of an ankle systolic blood pressure to a brachial systolic blood pressure. In this case, if the thus calculated blood-pressure index is smaller than 0.9, that is, if the ankle systolic blood pressure is smaller than the product of the brachial systolic blood pressure and 0.9, it can be judged that the subject is suspected of arteriostenosis.

As another sort of device for evaluating arteriosclerosis, there is known a pulse-wave-propagation-velocity-related-information obtaining device that obtains pulse-wave-propagation-velocity-related information, such as pulse-wave propagation velocity or pulse-wave. propagation time, that is related to a velocity at which a pulse wave propagates between two portions of a living subject. Japanese Patent Laid-Open Publication No. 8-257002 or its corresponding U.S. Pat. No. 5,743,856 discloses an example of the information obtaining device. Since pulse-wave-velocity-related information is influenced by calcification or arteriostenosis, the information can be used to evaluate arteriosclerosis. For example, pulse-wave propagation velocity as a sort of pulse-wave-velocity-related information is influenced by arteriosclerosis, such that the velocity increases as calcification advances, and decreases as the degree of arteriostenosis increases.

In many cases arteriostenosis occurs to an inferior-limb artery, but in some cases it occurs to a superior-limb artery. For example, it is known that the stenosis occurs to a subclavian artery. However, as described above, ankle-and-brachium blood-pressure index is calculated as the proportion of ankle blood pressure to brachial blood pressure. That is, whether the ankle blood pressure is abnormal is judged by comparing the ankle blood pressure with the brachial blood pressure. Therefore, based on the ankle-and-brachium blood-pressure index, it can be judged whether an artery between the heart and the ankle, in particular, an inferior-limb artery has stenosis. However, it is difficult to judge, based on the ankle-and-brachium blood-pressure index, whether a superior-limb artery has stenosis.

Hence, the Inventors propose, in a related application, an arteriostenosis inspecting apparatus that inspects arteriostenosis of a superior limb based on a left-and-right-superior-limb-blood-pressure ratio as a ratio between a left-superior-limb blood pressure and a right-superior-limb blood pressure. If an artery of a left or right superior limb suffers stenosis, blood pressure in the stenotic artery lowers. Therefore, a left-and-right-superior-limb-blood-pressure ratio obtained in the case where neither of the left and right superior limbs has arteriostenosis, differs from that obtained in the case where only one of the two superior limbs has the stenosis. Thus, based on the left-and-right-superior-limb-blood-pressure ratio, it can be judged whether a superior-limb artery has arteriostenosis.

However, in the case where an artery of a left or right superior limb has stenosis, the stenotic artery may simultaneously suffer advanced calcification. In this case, the stenosis may be overlooked by the inspection based on only the left-and-right-superior-limb-blood-pressure ratio. More specifically described, if an artery has stenosis, blood pressure should lower, because of the presence of the stenosis, on a downstream side of the stenotic portion of the artery. If, however, calcification occurs to the downstream-side portion of the artery where a cuff is worn, the blood pressure should increase because an additional pressure is needed to press or widen the hardened portion of the artery. Thus, if the blood-pressure increase caused by the calcification of the artery is equal to, or greater than, the blood-pressure decrease caused by the stenosis of the artery, the superior-limb blood pressure should apparently take a normal value and accordingly the left-and-right-superior-limb-blood-pressure ratio should apparently take a normal value.

In addition, as described above, pulse-wave propagation velocity increases as calcification advances, and decreases as the degree of arteriostenosis increases. That is, arteriostenosis and calcification influence pulse-wave propagation velocity in different manners. Therefore, if arteriostenosis and calcification simultaneously occur, pulse-wave propagation velocity may apparently take a normal value.

SUMMARY OF THE INVENTION

It is therefore an object of the present invention to provide an arteriosclerosis evaluating apparatus which can accurately evaluate degree of arteriosclerosis of a superior limb of a living subject.

The above object has been achieved by the present invention. According to the present invention, there is provided an arteriosclerosis evaluating apparatus, comprising a left-superior-limb-blood-pressure measuring device which measures, with a cuff, a left-superior-limb blood pressure of a left superior limb of a living subject; a right-superior-limb-blood-pressure measuring device which measures, with a cuff, a right-superior-limb blood pressure of a right superior limb of the subject; a left-and-right-superior-limb-blood-pressure-ratio determining means for determining a left-and-right-superior-limb blood-pressure ratio as a ratio between the left-superior-limb blood pressure measured by the leftsuperior-limb-blood-pressure measuring device and the right-superior-limb blood pressure measured by the right-superior-limb-blood-pressure measuring device; a pulse-wave-propagation-velocity-related-information obtaining device which obtains at least one set of pulse-wave-propagation-velocity-related information that is related to at least one velocity at which at least one pulse wave propagates in at least one of (a) a first body portion of the subject that includes at least a portion of the left superior limb and (b) a second body portion of the subject that includes at least a portion of the right superior limb; and a display device which displays the left-and-right-superior-limb blood-pressure ratio determined by the left-and-right-superior-limb-blood-pressure-ratio determining means, and the at least one set of pulse-wave-propagation-velocity-related information obtained by the pulse-wave-propagation-velocity-related-information obtaining device, such that the left-and-right-superior-limb blood-pressure ratio and the at least one set of pulse-wave-propagation-velocity-related information are comparable with each other by a person.

According to this invention, the left-and-right-superior-limb blood-pressure ratio is determined, and the at least one set of pulse-wave-propagation-velocity-related information is obtained from the at least one of (a) the first body portion of the subject that includes at least the portion of the left superior limb and (b) the second body portion of the subject that includes at least the portion of the right superior limb. In addition, the left-and-right-superior-limb blood-pressure ratio and the pulse-wave-propagation-velocity-related information are displayed by the display device, such that the left-and-right-superior-limb blood-pressure ratio and the pulse-wave-propagation-velocity-related information are comparable with each other by a person. Therefore, based on the comparison of the left-and-right-superior-limb blood-pressure ratio and the pulse-wave-propagation-velocity-related information with each other, the person can judge as follows: Even if the left-and-right-superior-limb blood-pressure ratio may not indicate the presence of arteriostenosis, but if the pulse-wave-propagation-velocity-related information indicates the presence of advanced calcification, then the person can judge that the blood-pressure decrease caused by the stenosis is offset by the blood-pressure increase by the calcification and accordingly the left-and-right-superior-limb blood-pressure ratio takes the apparently normal value, and therefore that the subject may suffer the stenosis. In addition, even if the pulse-wave-propagation-velocity-related information may fall in a normal range, but if the left-and-right-superior-limb blood-pressure ratio indicates the stenosis, then the person can judge that the change of pulse-wave-propagation-velocity-related information caused by the calcification is offset by the change of the information caused by the stenosis and accordingly the information takes the apparently normal value, and therefore that the subject may suffer the calcification.

Here, preferably, the pulse-wave-propagation-velocity-related-information obtaining device obtains the at least one set of pulse-wave-propagation-velocity-related information from the at least one of (a) the first body portion of the subject that includes at least the portion of the left superior limb and does not include the right superior limb and (b) the second body portion of the subject that includes at least the portion of the right superior limb and does not include the left superior limb. According to this feature, a set of pulse-wave-propagation-velocity-related information is influenced by arteriosclerosis of only one superior limb but is not influenced by arteriosclerosis of the other superior limb. Therefore, the person can accurately judge whether a portion of the one superior limb where a blood pressure is measured suffers calcification and, in the case where the left-and-right-superior-limb blood-pressure ratio indicates normalcy, the person can accurately judge whether the normalcy is because there is no arteriostenosis or because there are not only arteriosclerosis but also calcification.

Also, preferably, the pulse-wave-propagation-velocity-related-information obtaining device obtains the at least one set of pulse-wave-propagation-velocity-related information from the at least one of (a) the first body portion of the subject that includes at least the portion of the left superior limb where the left-superior-limb blood pressure is measured and (b) the second body portion of the subject that includes at least the portion of the right superior limb where the right-superior-limb blood pressure is measured. According to this feature, the person can accurately judge, based on a set of pulse-wave-propagation-velocity-related information, whether an arterial wall of a portion of a superior limb where a blood pressure is measured suffers calcification. Therefore, in the case where the left-and-right-superior-limb blood-pressure ratio indicates normalcy, the person can accurately judge whether the normalcy is because there is no arteriostenosis or because there are not only arteriosclerosis but also calcification.

Also, preferably, the pulse-wave-propagation-velocity-related-information obtaining device obtains a set of pulse-wave-propagation-velocity-related information from each one of (a) the first body portion of the subject that includes at least the portion of the left superior limb and does not include the right superior limb and (b) the second body portion of the subject that includes at least the portion of the right superior limb and does not include the left superior limb. According to this feature, each of the two sets of pulse-wave-propagation-velocity-related information is influenced by arteriosclerosis of only a corresponding one of the left and right superior limbs but is not influenced by arteriosclerosis of the other superior limb. Therefore, the person can accurately judge, based on each of the two sets of pulse-wave-propagation-velocity-related information, whether a portion of the corresponding one superior limb where a blood pressure is measured suffers calcification and, in the case where the left-and-right-superior-limb blood-pressure ratio indicates normalcy, the person can accurately judge whether the normalcy is because there is no arteriostenosis or because there are not only arteriosclerosis but also calcification.

Also, preferably, the pulse-wave-propagation-velocity-related-information obtaining device obtains the set of pulse-wave-propagation-velocity-related information from the each one of (a) the first body portion of the subject that includes at least the portion of the left superior limb where the left-superior-limb blood pressure is measured and (b) the second body portion of the subject that includes at least the portion of the right superior limb where the right-superior-limb blood pressure is measured. According to this feature, the person can accurately judge, based on each of the two sets of pulse-wave-propagation-velocity-related information, whether a portion of a corresponding one of the left and right superior limbs where a blood pressure is measured suffers calcification and, in the case where the left-and-right-superior-limb blood-pressure ratio indicates normalcy, the person can accurately judge whether the normalcy is because there is no arteriostenosis or because there are not only arteriosclerosis but also calcification.

BRIEF DESCRIPTION OF THE DRAWINGS

The above and optional objects, features, and advantages of the present invention will be better understood by reading the following detailed description of preferred embodiments of the invention when considered in conjunction with the drawings, in which.

DETAILED DESCRIPTION OF PREFERRED EMBODIMENTS

Figure 1:
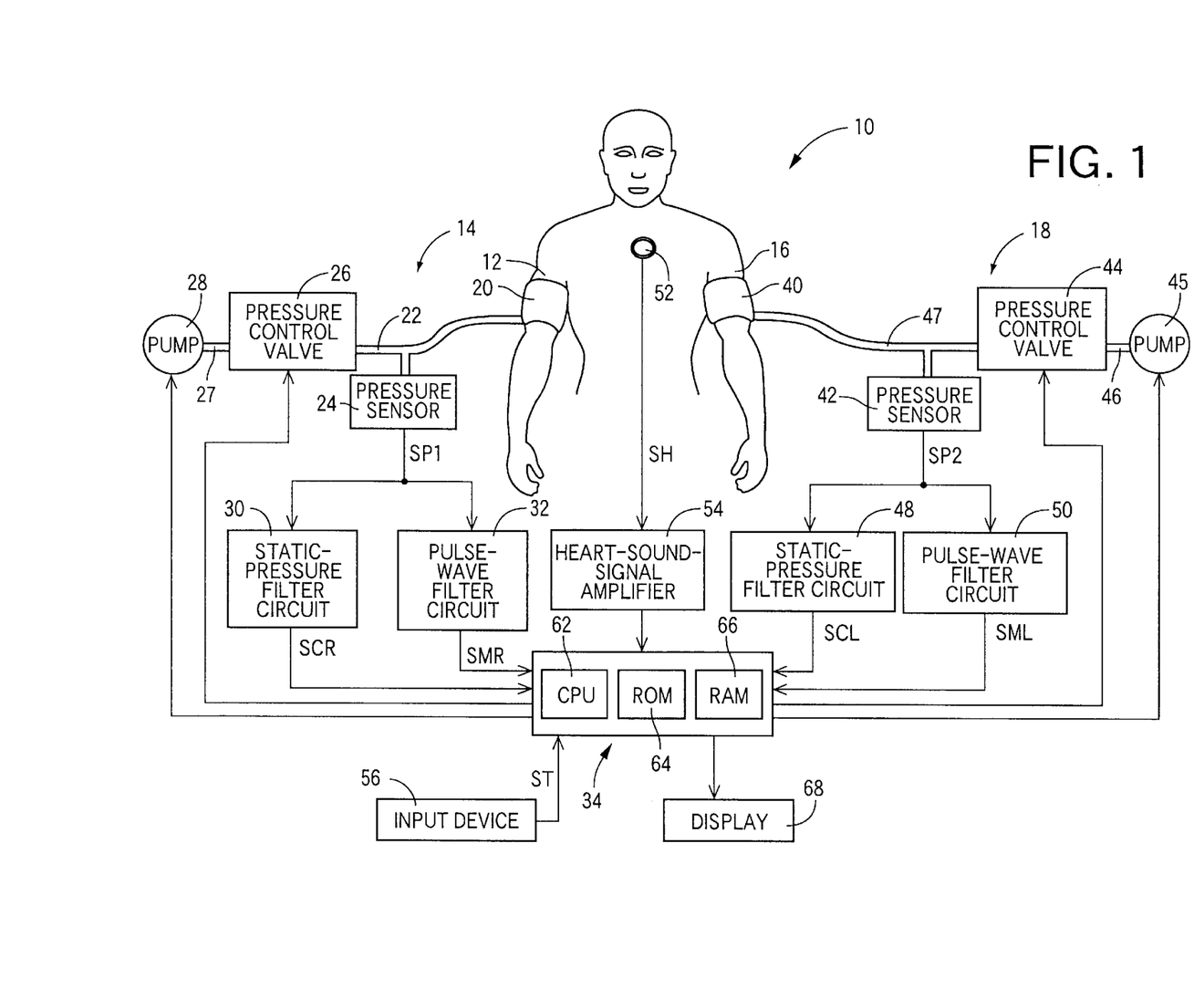
FIG. 1 is a diagrammatic view for explaining a construction of an arteriosclerosis evaluating apparatus to which the present invention is applied.

Hereinafter, there will be described a preferred embodiment of the present invention in detail by reference to the drawings. FIG. 1 shows a view for explaining a construction of an arteriosclerosis evaluating apparatus 10 to which the present invention is applied.

The arteriosclerosis evaluating apparatus 10 includes a right-brachium-blood-pressure measuring device 14 which measures a blood pressure of a right brachium 12 of a living subject and functions as a right-superior-limb-blood-pressure measuring device; and a left-brachium-blood-pressure measuring device 18 which measures a blood pressure of a left brachium 16 of the subject and functions as a left-superior-limb-blood-pressure measuring device.

The right-brachium-blood-pressure measuring device 14 includes a cuff 20 which includes a belt-like cloth bag and a rubber bag accommodated in the cloth bag and which is adapted to be worn on the right brachium 12. The cuff 20 is connected via a piping 22 to a pressure sensor 24 and a pressure control valve 26. The pressure control valve 26 is connected via a piping 27 to an air pump 28. The pressure sensor 24 supplies a first pressure signal SP1 to a static-pressure filter circuit 30 and a pulse-wave filter circuit 32. The measuring device 14 additionally includes an electronic control device 34.

The pressure control valve 26 adjusts a pressure of a pressurized air supplied from the air pump 28, and supplies the pressure-adjusted air to the cuff 20, or discharges the pressurized air from the cuff 20, so as to control an air pressure in the cuff 20.

The pressure sensor 24 detects the air pressure in the cuff 20, and supplies the first pressure signal SP1 representing the detected air pressure, to each of the static-pressure filter circuit 30 and the pulse-wave filter circuit 32. The static-pressure filter circuit 30 includes a low-pass filter which extracts, from the first pressure signal SP1, a right-brachium cuff-pressure signal $SC_R$ representing a static component of the detected air pressure, i.e., a pressing pressure of the cuff 20 (hereinafter, referred to as the right-brachium cuff pressure $PC_R$). The filter circuit 30 supplies the right-brachium cuff-pressure signal $SC_R$ to the electronic control device 34 via an A/D (analog-to-digital) converter, not shown.

The pulse-wave filter circuit 32 includes a band-pass filter which extracts, from the first pressure signal SP1, a right-brachium pulse-wave signal $SM_R$ representing an oscillatory component of the detected air pressure that has specific frequencies. The filter circuit 32 supplies the right-brachium pulse-wave signal $SM_R$ to the electronic control device 32 via an A/D converter, not shown. The right-brachium pulse-wave signal $SM_R$ represents a right-brachium pulse wave as a pressure oscillation that is transmitted from a right brachial artery of the subject to the cuff 20.

The left-brachium-blood-pressure measuring device 18 includes a cuff 40, a pressure sensor 42, a pressure control valve 44, an air pump 45, a static-pressure filter circuit 48, and a pulse-wave filter circuit 50 that have respective arrangements identical with those of the counterparts 20, 24, 26, 28, 30, 32 of the above-described right-brachium-blood-pressure measuring device 14; and additionally includes the electronic control device 34.

The cuff 40 is adapted to be worn on the left brachium 16. The pressure control valve 44 and the air pump 45 are connected to each other via a piping 46; and the cuff 40, the pressure sensor 42, and the pressure control valve 44 are connected to each other via a piping 47. The pressure sensor 42 supplies a second pressure signal SP1 representing an air pressure in the cuff 40, to each of the static-pressure filter circuit 48 and the pulse-wave filter circuit 50. The static-pressure filter circuit 48 extracts, from the second pressure signal SP2, a left-brachium cuff-pressure signal $SC_L$ representing a static component of the detected air pressure, i.e., a pressing pressure of the cuff 40 (hereinafter, referred to as the left-brachium cuff pressure $PC_L$). The filter circuit 48 supplies the left-brachium cuff-pressure signal $SC_L$ to the electronic control device 34 via an A/D converter, not shown. The pulse-wave filter circuit 50 extracts, from the second pressure signal SP2, a left-brachium pulse-wave signal $SM_L$ representing an oscillatory component of the detected air pressure that has specific frequencies. The filter circuit 50 supplies the left-brachium pulse-wave signal $SM_L$ to the electronic control device 34 via an A/D converter, not shown. The left-brachium pulse-wave signal $SM_L$ represents a left-brachium pulse wave as a pressure oscillation that is transmitted from a left brachial artery of the subject to the cuff 40.

heart-sound microphone 52 is attached, with, e.g., an adhesive tape, not shown, to a chest of the patient. The heart-sound microphone 52 functions as a heartbeat-synchronous-signal detecting device which detects a heart sound as a heartbeat-synchronous signal. The microphone 52 incorporates a piezoelectric element, not shown, which converts a heart sound produced from the heart of the subject, into an electric signal, i.e., a heart-sound signal SH. A heart-sound-signal amplifier 54 incorporates four sorts of filters, not shown, which cooperate with each other to attenuate a low-pitch component of the heart sound that has a great energy, so as to allow good recording of a high-pitch component of the heart sound. The heart-sound signal SH supplied from the heart-sound microphone 52 is amplified and filtered by the heart-sound-signal amplifier 54, and then is supplied to the electronic control device 34 via an A/D converter, not shown.

An input device 56 includes a plurality of numeric keys, not shown, which are operable for inputting a number representing a stature T of the subject, and supplies a stature signal ST representing the subject's stature T inputted through the numeric keys, to the electronic control device 34.

The electronic control device 34 is provided by a so-called microcomputer including a CPU (central processing unit) 62, a ROM (read only memory) 64, a RAM (random access memory) 66, and an I/O (input-and-output) port, not shown. The CPU 62 processes signals according to control programs pre-stored in the ROM 64, while utilizing a temporary-storage function of the RAM 66. The CPU 62 outputs, from the I/O port, drive signals to the air pumps 28, 45 and the pressure control valves 26, 44, so as to control the respective air pressures in the cuffs 20, 40. In addition, the CPU 62 processes the signals supplied to the control device 34, so as to calculate a left-and-right-superior-limb blood-pressure ratio BBI, and left and right pulse-wave propagation velocities $PWV_L$, $PWV_R$, of the subject, and operates a display device 68 such as a CRT (cathode ray tube) to display the thus calculated values such that those values can be compared with each other by an observer such as a doctor.

Figure 2:
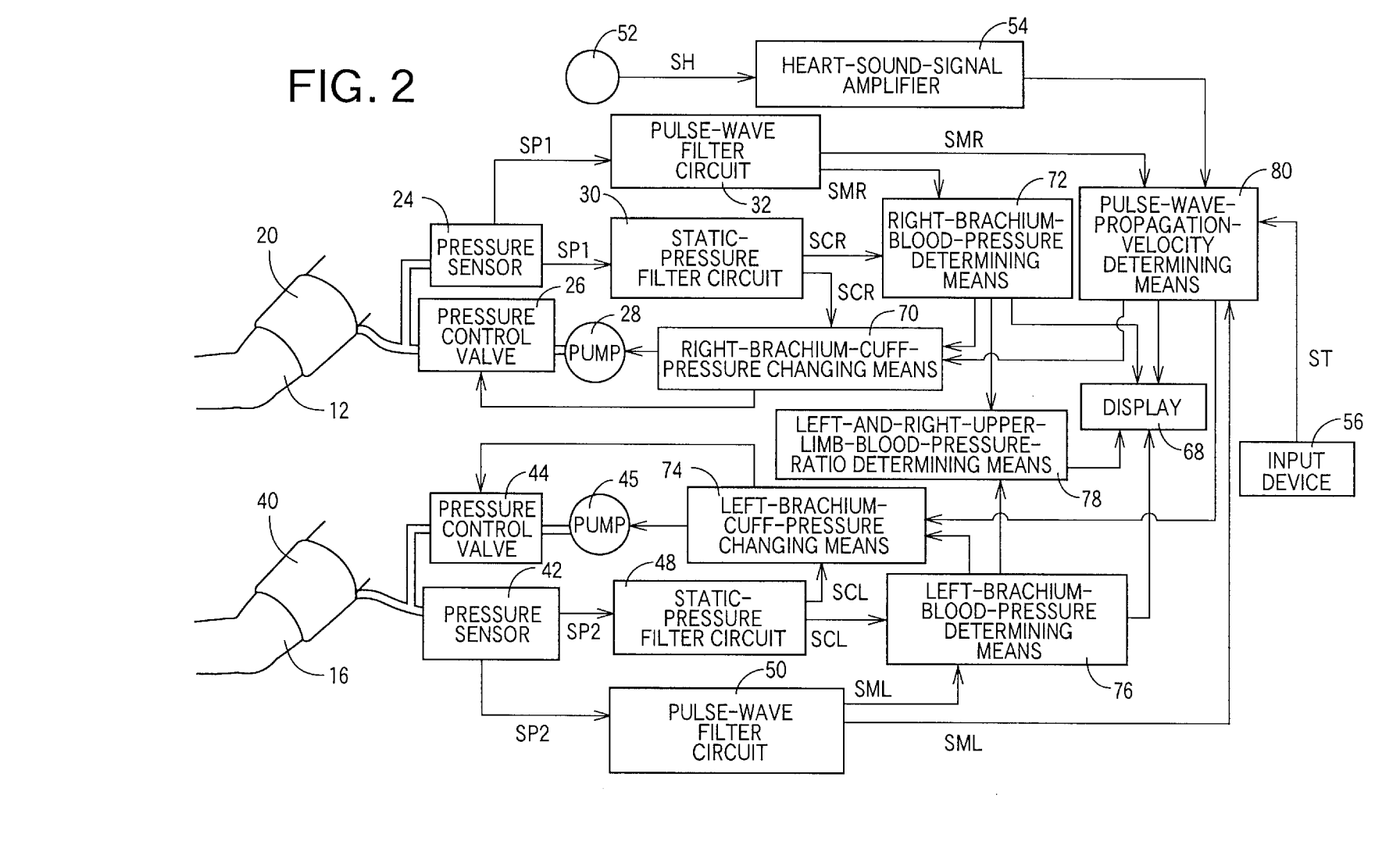
FIG. 2 is a diagrammatic view for explaining essential control functions of an electronic control device of the arteriosclerosis evaluating apparatus of FIG. 1.

FIG. 2 is a diagrammatic view for explaining essential control functions of the electronic control device 34. A right-brachium-cuff-pressure changing device or means 70 controls, according to a command signal supplied from a right-brachium-blood-pressure determining device or means 72, described below, and based on the right-brachium-cuff-pressure signal $SC_R$ supplied from the static-pressure filter circuit 30, the air pump 28 and the pressure control valve 26 connected to the same 28, so as to change the right-brachium cuff pressure $PC_R$, as follows: First, the right-brachium cuff pressure $PC_R$ is quickly increased up to a prescribed target pressure value $PC_M$ (e.g., 180 mmHg) that would be higher than a systolic blood pressure $PBR_{SYS}$ of the right brachium 12, and then the right-brachium cuff pressure $PC_R$ is slowly decreased at a rate of about 3 mmHg/sec. After a right-brachium diastolic blood pressure $BPR_{DIA}$ is determined, the right-brachium cuff pressures $PC_R$ is released to an atmospheric pressure.

In addition, the right-brachium-cuff-pressure changing means 70 controls, according to a command signal supplied from a pulse-wave-propagation-velocity determining device or means 80, described later, and based on the right-brachium-cuff-pressure signal $SC_R$ supplied from the static-pressure filter circuit 30, the air pump 28 and the pressure control valve 26 connected to the same 28, so as to change the right-brachium cuff pressure $PC_R$ to a prescribed pulse-wave detection pressure. Here, the pulse-wave detection pressure is expected to be lower than the diastolic blood pressure $PBR_{DIA}$ of the right brachium 12 where the cuff 12 is worn, and assures that the right-brachium-pulse-wave signal $SM_R$ supplied from the pulse-wave filter circuit 32 has a sufficiently great magnitude. The pulse-wave detection pressure is prescribed at, e.g., 50 mmHg.

The right-brachium-blood-pressure determining means 72 determines the change of the right-brachium cuff pressure $PC_R$ represented by the right-brachium-cuff-pressure signal $SC_R$ continuously supplied from the static-pressure filter circuit 30 during the slow decreasing of the right-brachium cuff pressure $PC_R$ under the control of the right-brachium-cuff-pressure changing means 70, and the change of respective amplitudes of successive heartbeat-synchronous pulses of the right-brachium pulse wave represented by the right-brachium-pulse-wave signal $SM_R$ continuously supplied from the pulse-wave filter circuit 32 during the slow decreasing of the right-brachium cuff pressure $PC_R$. Then, based on the thus determined changes of the right-brachium cuff pressure $PC_R$ and the respective amplitudes of successive pulses of the right-brachium pulse wave, the determining means 72 determines blood-pressure values of the right brachium 12, i.e., a right-brachium systolic blood pressure $BPR_{SYS}$, a right-brachium diastolic blood pressure $BPR_{DIA}$, and a right-brachium mean blood pressure $BPR_{MEAN}$, according to a well-known oscillometric algorithm. In addition, the determining means 72 operates the display device 68 to display the thus determined right-brachium blood-pressure values BPR.

A left-brachium-cuff-pressure changing device or means 74 controls, according to a command signal supplied from a left-brachium-blood-pressure determining device or means 76, described below, and based on the left-brachium-cuff-pressure signal $SC_L$ supplied from the static-pressure filter circuit 48, the air pump 45 and the pressure control valve 44 connected to the same 45, so as to change the left-brachium cuff pressure $PC_L$ in the same manner as the manner in which the right-brachium-cuff-pressure changing means 70 changes the right-brachium cuff pressure $PC_R$. That is, first, the left-brachium cuff pressure $PC_L$ is quickly increased up to the above-described target pressure value $PC_M$, and then the left-brachium cuff pressure $PC_L$ is slowly decreased at the rate of about 3 mmHg/sec. After a left-brachium diastolic blood pressure $BPL_{DIA}$ is determined, the left-brachium cuff pressures $PC_L$ is released to an atmospheric pressure.

In addition, the left-brachium-cuff-pressure changing means 74 controls, according to a command signal supplied from the pulse-wave-propagation-velocity determining means 80, described later, and based on the left-brachium-cuff-pressure signal $SC_L$ supplied from the static-pressure filter circuit 48, the air pump 45 and the pressure control valve 44 connected to the same 45, so as to change the left-brachium cuff pressure $PC_L$ to the above-described pulse-wave detection pressure.

The left-brachium-blood-pressure determining means 76 determines the change of the left-brachium cuff pressure $PC_L$ represented by the left-brachium-cuff-pressure signal $SC_L$ continuously supplied from the static-pressure filter circuit 48 during the slow decreasing of the left-brachium cuff pressure $PC_L$ under the control of the left-brachium-cuff-pressure changing means 74, and the change of respective amplitudes of successive heartbeat-synchronous pulses of the left-brachium pulse wave represented by the left-brachium-pulse-wave signal $SM_L$ continuously supplied from the pulse-wave filter circuit 50 during the slow decreasing of the left-brachium cuff pressure $PC_L$. Then, based on the thus determined changes of the left-brachium cuff pressure $PC_L$ and the respective amplitudes of successive pulses of the left-brachium pulse wave, the determining means 76 determines blood-pressure values of the left brachium 16, i.e., a left-brachium systolic blood pressure $BPL_{SYS}$, a left-brachium diastolic blood pressure $BPL_{DIA}$, and a left-brachium mean blood pressure $BPL_{MEAN}$, according to the well-known oscillometric algorithm. In addition, the determining means 76 operates the display device 68 to display the thus determined left-brachium blood-pressure values BPL.

A left-and-right-superior-limb-blood-pressure-ratio calculating device or means 78 calculates a left-and-right-superior-limb blood-pressure ratio BBI as a ratio between the left-brachium blood pressure BPL determined by the left-brachium-blood-pressure determining means 76 and the right-brachium blood pressure BPR determined by the right-brachium-blood-pressure determining means 72. In addition, the calculating means 78 operates the display device 68 to display the thus calculated left-and-right-superior-limb blood-pressure ratio BBI. The left-and-right-superior-limb blood-pressure ratio BBI may be a ratio between the left and right systolic blood pressure $BBL_{SYS}$, $BBR_{SYS}$, a ratio between the left and right mean blood pressure $BBL_{MEAN}$, $BBR_{MEAN}$, or a ratio between the left and right diastolic blood pressure $BBL_{DIA}$, $BBR_{DIA}$, and the higher one of the left-brachium blood pressure BPL and the right-brachium blood pressure BPR is used as a denominator of the ratio BBI and the lower one is used as a numerator of the same BBI.

A pulse-wave-prop agation-velocity determining device or means 80 as a portion of pulse-wave-propagationvelocity-related-information obtaining device or means determines, based on the right-brachium-pulse-wave signal $SM_R$ and the left-brachium-pulse-wave signal $SM_L$ respectively supplied from the two static-pressure filter circuits 32, 50, and the heart-sound-signal SH supplied from the heart-sound-signal amplifier 54, a pulse-wave propagation time (hereinafter, referred to as a right pulse-wave propagation time $DT_R$) in which a pulse wave propagates through a right body portion of the subject that is located between the heart and the right brachium 12, includes a portion where the right brachium blood pressure values BPR are measured, and does not include the left brachium 16, and a pulse-wave propagation time (hereinafter, referred to as a left pulse-wave propagation time $DT_L$) in which a pulse wave propagates through a left body portion of the subject that is located between the heart and the left brachium 16, includes a portion where the left brachium blood pressure values BPL are measured, and does not include the right brachium 12. Then, the determining means 80 substitutes the subject's stature T represented by the stature signal ST supplied from the input device 56, with the following Expression 1 representing a relationship between stature T and propagation distance L, pre-stored in the ROM 64:

$$L = aT + b \quad \text{(Expression 1)}$$

where a and b are experimentally determined constants. Thus, the determining means 80 determines the propagation distance L between the heart and each of the right and left brachia 12, 16. In addition, the determining means 80 substitutes the propagation distance L and the right pulse-wave propagation time $DT_R$ with the following Expression 2, so as to calculate a right pulse-wave propagation velocity $PWV_R$ (cm/sec), and substitutes the propagation distance L and the left pulse-wave propagation time $DT_L$ with Expression 2, so as to calculate a left pulse-wave propagation velocity $PWV_L$ (cm/sec):

$$PWV = L/DT \quad \text{(Expression 2)}$$

Finally, the determining means 80 operates the display device 68 to display the thus calculated right and left pulse-wave propagation velocities $PWV_R$, $PWV_L$ together with the left-and-right-superior-limb blood-pressure ratio BBI.

In the arteriosclerosis evaluating apparatus 10, the pulse-wave-propagation-velocity-related-information obtaining device includes not only the pulse-wave-propagation-velocity determining means 80, but also the cuffs 20, 40, the pressure sensors 24, 42, the pressure control valves 26, 44, the air pumps 28, 45, the pulse-wave filter circuits 32, 50, and the input device 56 that are used to obtain the right-brachium-pulse-wave signal $SM_R$, the left-brachium-pulse-wave signal $SM_L$, and the heart-sound signal SH that are used by the determining means 80 to determine the right pulse-wave propagation velocity $PWV_R$ and the left pulse-wave propagation velocity $PWV_L$.

Figure 3:
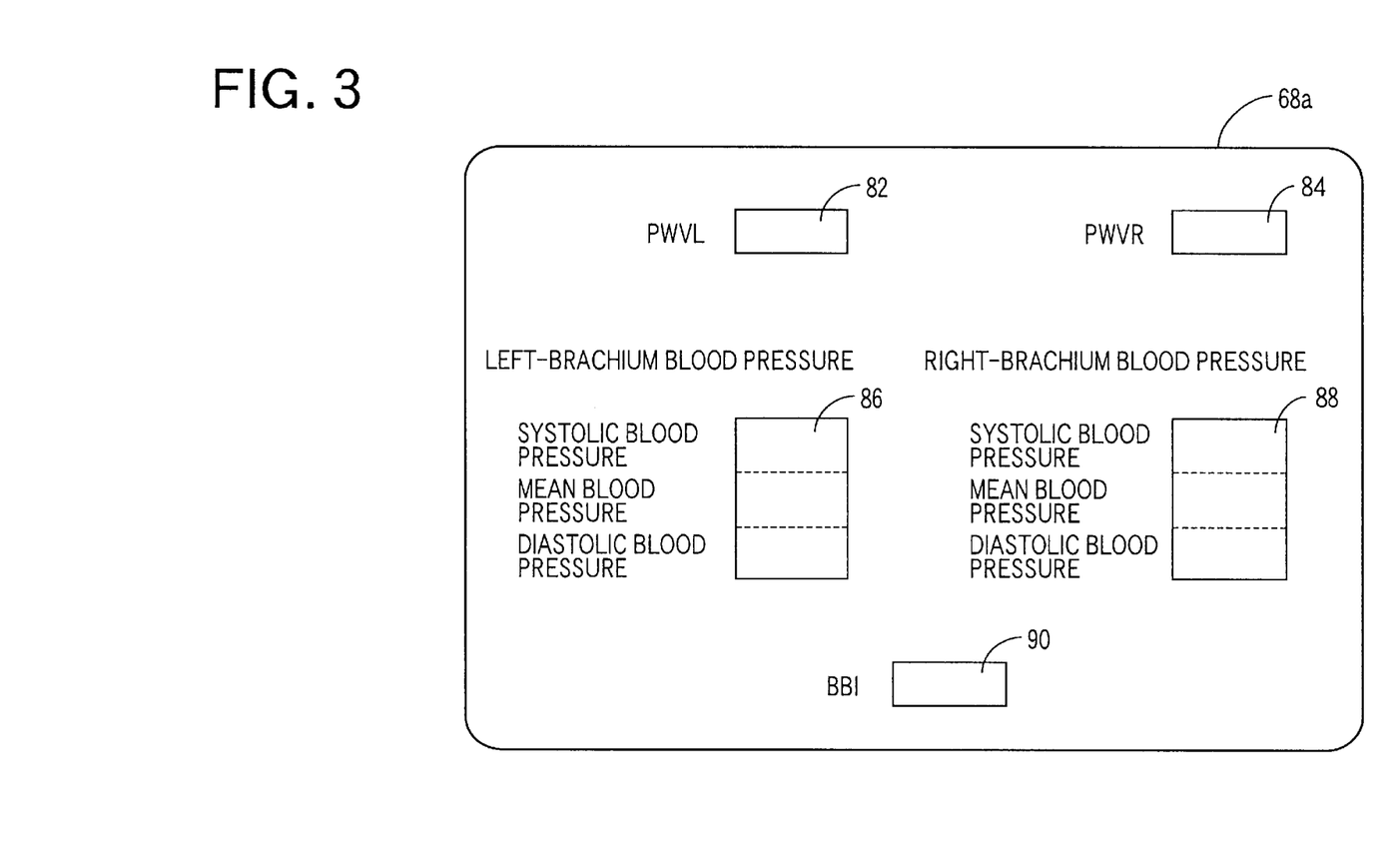
FIG. 3 is a view showing an example of a screen image displayed by a display device shown in FIG. 1.

FIG. 3 is a view showing an example of an image screen 68a of the display device 68. The image screen 68a includes a left-pulse-wave-propagation-velocity display area 82 for displaying the left pulse-wave propagation velocity $PWV_L$; a right-pulse-wave-propagation-velocity display area 84 for displaying the right pulse-wave propagation velocity $PWV_R$; a left-brachium-blood-pressure display area 86 for displaying the left-brachium blood-pressure values BPL; a right-brachium-blood-pressure display area 88 for displaying the right-brachium blood-pressure values BPR; and a left-and-right-superior-limb-blood-pressure-ratio display area 90 for displaying the left-andright-superior-limb blood-pressure ratio BBI.

When the display device 68 displays the left-and-right-superior-limb blood-pressure ratio BBI, the left pulse-wave propagation velocity $PWV_L$, and the right pulse-wave propagation velocity $PWV_R$, first, a person can judge, from the left-and-right-superior-limb blood-pressure ratio BBI, as follows: If the left-and-right-superior-limb blood-pressure ratio BBI is near to 1, the person can understand that the left-brachium systolic blood pressure $BPL_{SYS}$ and the right-brachium systolic blood pressure $BPL_{SYS}$ are near to each other, and judge that neither of the left and right superior-limb arteries would probably have stenosis. On the other hand, if the left-and-right-superior-limb blood-pressure ratio BBI is smaller than a prescribed standard value, e.g., 0.9, the person can understand that either one of the left and right systolic blood pressure $BPL_{SYS}$, $BPL_{SYS}$ is considerably lower than the other systolic blood pressure, and judge that the blood pressure would be low because there would be arteriostenosis in a body portion on an upstream side of a left or right body portion where blood pressure values are measured.

In addition, from the left pulse-wave propagation velocity $PWV_L$ and the right pulse-wave propagation velocity $PWV_R$, the person can determine a degree of arteriosclerosis present between the heart and the left brachium 16, and a degree of arteriosclerosis present between the heart and the right brachium 12. For example, if the left pulse-wave propagation velocity $PWV_L$ is very fast, the person can understand that a portion or an entirety of an artery between the heart and the body portion where the cuff 40 is worn suffers advanced calcification. On the other hand, if the left pulse-wave propagation velocity $PWV_L$ is slower than a normal value, the person can judge that there would probably be arteriostenosis between the heart and the body portion where the cuff 40 is worn. Moreover, even if the person may not judge the presence of arteriostenosis based on each pulse-wave propagation velocity PWV only, the person can judge, if the left-and-right-superior-limb blood-pressure ratio BBI indicates the presence of arteriostenosis, which one of the left and right superior limbs suffers the stenosis, by comparing the left and right pulse-wave propagation velocities $PWV_L$, $PWV_R$ with each other.

Furthermore, if at least one of the left and right pulse-wave propagation velocities $PWV_L$, $PWV_R$ indicates the presence of advanced calcification, the person can judge, even if the left-and-right-superior-limb blood-pressure ratio BBI may be normal, that a blood-pressure decrease caused by arteriostenosis would be off-set by a blood-pressure increase caused by the calcification and consequently the blood-pressure ratio BBI would take the apparently normal value, and that the body portion suffering the calcification would also suffer the stenosis.

In addition, even if the left or right pulse-wave propagation velocity $PWV_L$, $PWV_R$ may be normal, the person can judge, if the left-and-right-superior-limb blood-pressure ratio BBI indicates the presence of advanced arteriosclerosis, that a decrease of pulse-wave propagation velocity PWV caused by calcification would be off-set by an increase of pulse-wave propagation velocity PWV caused by the stenosis and consequently the pulse-wave propagation velocity PWV would take the apparently normal value, and that the superior limb exhibiting the normal pulse-wave propagation velocity PWV would suffer both the calcification and the stenosis.

Figure 4:
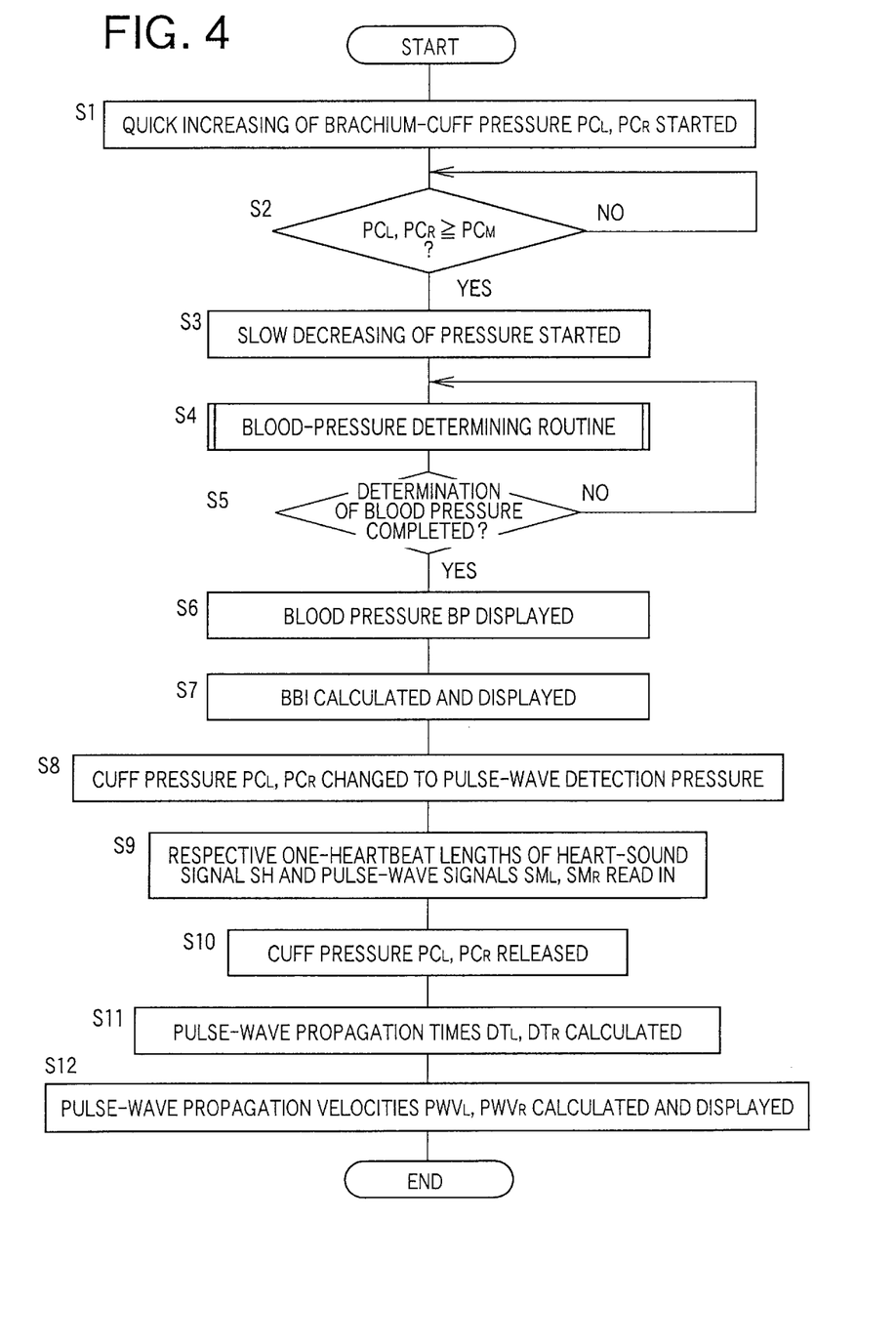
FIG. 4 is a flow chart representing the essential control functions of the electronic control device, shown in the diagrammatic view of FIG. 2.

FIG. 4 shows a flow chart for explaining the essential control functions of the electronic control device 34, shown in the diagrammatic view of FIG. 2. This flow chart is started when a start button, not shown, is operated, on the assumption that the stature signal ST has already been supplied from the input device 56.

First, at Step S1 (hereinafter, "Step" is omitted), the control device operates the two air pumps 28, 45 and the two pressure control valves 26, 44 so as to start quick increasing of the right-brachium cuff pressure $PC_R$ and the left-brachium cuff pressure $PC_L$. Subsequently, at S2, the control device judges whether both of the right-brachium cuff pressure $PC_R$ and the left-brachium cuff pressure $PC_L$ have reached the prescribed target pressure value $PC_M$, e.g., 180 mmHg. If a negative judgment is made at S2, S2 is repeated On the other hand, if a positive judgment is made at S2, the control goes to S3 to stop the air pumps 28, 45 and operate the pressure control valves 26, 44 so as to start slow decreasing of the right-brachium cuff pressure $PC_R$ and the left-brachium cuff pressure $PC_L$ at the prescribed rate of about 3 mmHg/sec.

Then, the control goes to S4 through S6 corresponding to the right-brachium-blood-pressure determining means 72 and the left-brachium-blood-pressure determining means 76. First, at S4, the control device carries out a blood-pressure determining routine. More specifically described, the control device determines respective amplitudes of respective heartbeat-synchronous pulses of the right-brachium pulse wave represented by the right-brachium-pulse-wave signal $SM_R$ continuously supplied from the pulse-wave filter circuit 32, and respective values of the right-brachium cuff pressure $PC_R$, represented by the right-brachium-cuff-pressure signal $SC_R$ continuously supplied from the static-pressure filter circuit 30, at respective times of detection of the respective pulses of the right-brachium pulse wave. Based on the change of the amplitudes and the respective values of the right-brachium cuff pressure $PC_R$, the control device determines a right-brachium systolic blood pressure $BPR_{SYS}$, a right-brachium mean blood pressure $BPR_{MEAN}$, and a right-brachium diastolic blood pressure $BPR_{DIA}$, according to a well-known oscillometric blood-pressure determining algorithm. Similarly, the control device determines left-brachium blood pressure values BPL. More specifically described, the control device determines respective amplitudes of respective heartbeat-synchronous pulses of the left-brachium pulse wave represented by the right-brachium-pulse-wave signal $SM_L$ continuously supplied from the pulse-wave filter circuit 50, and respective values of the left-brachium cuff pressure $PC_L$, represented by the left-brachium-cuff-pressure signal $SC_L$ continuously supplied from the static-pressure filter circuit 48, at respective times of detection of the respective pulses of the left-brachium pulse wave. Based on the change of the amplitudes and the respective values of the left-brachium cuff pressure $PC_L$, the control device determines a left-brachium systolic blood pressure $BPL_{SYS}$, a left-brachium mean blood pressure $BPL_{MEAN}$, and a left-brachium diastolic blood pressure $BPL_{DIA}$.

Subsequently, at S5, the control device judges whether the determination of blood-pressure values has been completed. If a negative judgment is made at S, S4 is repeated. Meanwhile, if a positive judgment is made at S5, the control goes to S6 to operate the display device 68 to display the left-brachium blood-pressure values BPL and the right-brachium blood-pressure values BPR, determined at S4, in the left-brachium-blood-pressure display area 86 and the right-brachium-blood-pressure display area 88 of the image screen 68a, respectively.

Then, the control goes to S7 corresponding to the left-and-right-superior-limb-blood-pressure-ratio calculating means 78. At S7, the control device calculates a left-and-right-superior-limb blood-pressure ratio BBI between the left-brachium blood-pressure value BPL and the right-brachium blood-pressure value BPR, each determined at S4. The left-brachium blood-pressure value BPL may be any one of the left-brachium systolic, mean, and diastolic blood-pressure values, and the right-brachium blood-pressure value BPR may be any one of the right-brachium systolic, mean, and diastolic blood-pressure values. For example, the left-brachium and right-brachium systolic blood-pressure values $BPL_{SYS}$, $BPR_{SYS}$ may be used. In addition, the higher one of the two systolic blood-pressure values $BPL_{SYS}$, $BPR_{SYS}$ is used as a denominator of the left-and-right-superior-limb blood-pressure ratio BBI; and the lower one of the two systolic blood-pressure values $BPL_{SYS}$, $BPR_{SYS}$ is used as a numerator of the blood-pressure ratio BBI. Then, the control device operates the display device 68 to display the thus calculated left-and-right-superior-limb blood-pressure ratio BBI in the left-and-right-superior-limb-blood-pressure-ratio display area 90 of the image screen 68a.

Subsequently, at S8, the control device again starts the air pumps 28, 45 and operates the pressure control valves 26, 44 so as to change both of the right-brachium cuff pressure $PC_R$ and the left-brachium cuff pressure $PC_L$ to the prescribed pulse-wave detection pressure, e.g., 50 mmHg.

Then, at S9, the control device reads in respective one-heartbeat lengths of the right-brachium-pulse-wave signal $SM_R$ supplied from the static-pressure filter circuit 32, the left-brachium-pulse-wave signal $SM_L$ supplied from the static-pressure filter circuit 50, and the heart-sound-signal SH supplied from the heart-sound microphone 52 via the heart-sound-signal amplifier 54. Then, the control goes to S10 to stop the air pumps 28, 45 and operate the pressure control valves 26, 44 so as to release each of the right-brachium cuff pressure $PC_R$ and the left-brachium cuff pressure $PC_L$ to an atmospheric pressure. In the flow chart shown in FIG. 4, S1 through S3, S8, and S10 correspond to the right-brachium-cuff-pressure changing means 70 and the left-brachium-cuff-pressure changing means 74.

Subsequently, the control goes to S11 and S12 corresponding to the pulse-wave-propagation-velocity determining means 80. First, at S11, the control device determines, based on the respective one-heartbeat lengths of the right-brachium-pulse-wave signal $SM_R$, the left-brachium-pulse-wave signal $SM_L$, and the heart-sound-signal SH, each read in at S9, a prescribed portion (e.g., a rising point or a notch point) of each of the left-brachium and right-brachium pulse waves and a corresponding prescribed portion (e.g., a start point of first heart sound I or a start point of second heart sound II) of the heart-sound waveform. Then, the control device determines, as a left pulse-wave propagation time $DT_L$, a time difference between a time of detection of the prescribed portion of the left-brachium pulse wave and a time of detection of the prescribed portion of the heart-sound waveform, and additionally determines, as a right pulse-wave propagation time $DT_R$, a time difference between a time of detection of the prescribed portion of the right-brachium pulse wave and a time of detection of the prescribed portion of the heart-sound waveform.

Subsequently, at S12, the control device substitutes the stature T represented by the stature signal ST already supplied thereto, with the above-indicated Expression 1, so as to determine a propagation distance L. In addition, the control device substitutes the propagation distance L, and the left or right pulse-wave propagation time $DT_L$, $DT_R$, determined at S11, with the above-indicated Expression 2, so as to calculate a left pulse-wave propagation velocity $PWV_L$ and a right pulse-wave propagation velocity $PWV_R$.

Then, the control device operates the display device 68 to display the thus calculated left and right pulse-wave propagation velocities $PWV_L$, $PWV_R$ in the left-pulse-wave-propagation-velocity display area 82 and the right-pulse-wave-propagation-velocity display area 84 of the image screen 68a, respectively.

In the above-described arteriosclerosis evaluating apparatus 10, the left-and-right-superior-limb blood-pressure ratio BBI is determined, the left pulse-wave propagation velocity $PWV_L$ is measured from the body portion between the heart and the left brachium 16, and the right pulse-wave propagation velocity $PWV_R$ is measured from the body portion between the heart and the right brachium 12. In addition, the left-and-right-superior-limb blood-pressure ratio BBI, the left pulse-wave propagation velocity $PWV_L$, and the right pulse-wave propagation velocity $PWV_R$ are displayed by the display device 68, such that the blood-pressure ratio BBI and the left and right pulse-wave propagation velocities $PWV_L$, $PWV_R$ are comparable with each other by the person. Therefore, based on the comparison of the left-and-right-superior-limb blood-pressure ratio BBI and the pulse-wave propagation velocity $PWV_L$, $PWV_R$ with each other, the person can judge as follows: Even if the left-and-right-superior-limb blood-pressure ratio BBI may not indicate the presence of arteriostenosis, but if the pulse-wave propagation velocity $PWV_L$, $PWV_R$ indicates the presence of advanced calcification, then the person can judge that the blood-pressure decrease caused by the stenosis is offset by the blood-pressure increase by the calcification and accordingly the blood-pressure ratio BBI takes the apparently normal value, and therefore that the subject would suffer the stenosis. In addition, even if the pulse-wave propagation velocity $PWV_L$, $PWV_R$ may fall in a normal range, but if the left-and-right-superior-limb blood-pressure ratio BBI indicates arteriostenosis, then the person can judge that the increase of pulse-wave propagation velocity $PWV_L$, $PWV_R$ caused by calcification is offset by the decrease of pulse-wave propagation velocity $PWV_L$, $PWV_R$ caused by the stenosis and accordingly the information takes the apparently normal value, and therefore that the subject would suffer advanced calcification.

In addition, in the above-described arteriosclerosis evaluating apparatus 10, the left pulse-wave propagation velocity $PWV_L$ is measured from the body portion between the heart and the left brachium 16, and the right pulse-wave propagation velocity $PWV_R$ is measured from the body portion between the heart and the right brachium 12. According to this feature, each of the two pulse-wave propagation velocities $PWV_L$, $PWV_R$ is influenced by arteriosclerosis of only a corresponding one of the two superior limbs but is not influenced by arteriosclerosis of the other superior limb. Therefore, the person can accurately judge, based on each of the two pulse-wave propagation velocities $PWV_L$, $PWV_R$, whether a portion of the corresponding one superior limb where a blood pressure is measured suffers calcification and, in the case where the left-and-right-superior-limb blood-pressure ratio BBI indicates normalcy, the person can accurately judge whether the normalcy is because there is no arteriostenosis or because there are not only arteriosclerosis but also calcification.

In addition, in the above-described arteriosclerosis evaluating apparatus 10, the right pulse-wave propagation velocity $PWV_R$ is measured from the body portion including the portion of the right brachium 12 where the right-brachium blood pressure BPR is measured, and the left pulse-wave propagation velocity $PWV_L$ is measured from the body portion including the portion of the left brachium 16 where the left-brachium blood pressure BPL is measured. According to this feature, the person can more accurately judge, based on each of the pulse-wave propagation velocity $PWV_R$, $PWV_L$, whether the portion of the corresponding brachium 12, 16 where the corresponding brachium blood pressure BPR, BPL is measured suffers calcification. Therefore, in the case where the left-and-right-superior-limb blood-pressure ratio BBI indicates normalcy, the person can more accurately judge whether the normalcy is because there is no arteriostenosis or because there are not only arteriosclerosis but also calcification.

While the present invention has been described in detail in its embodiment by reference to the drawings, it is to be understood that the invention may otherwise be embodied.

For example, in the above-described arteriosclerosis evaluating apparatus 10, the two pulse-wave propagation velocities PWV, i.e., the left and right pulse-wave propagation velocities $PWV_L$, $PWV_R$ are measured. However, it is possible to measure only one of the two pulse-wave propagation velocities PWV. In the latter case, if the one pulse-wave propagation velocity PWV indicates the presence of advanced calcification, the person can judge, even if the left-and-right-superior-limb blood-pressure ratio BBI may take an apparently normal value, that there would be arteriostenosis.

The body portions from which the pulse-wave propagation velocities PWV are measured, are not limited to the above-described portions. For example, it is possible to measure a pulse-wave propagation velocity PWV from a body portion between the left brachium 16 (or the right brachium) and an ankle (or a femoral portion), a body portion between the left brachium 16 (or the right brachium) and a cervical portion, a body portion between the left brachium 16 and a left wrist, a body portion between the right brachium 12 and a right wrist, a body portion between the left brachium 16 and a right wrist, or a body portion between the right brachium 12 and a left wrist.

In addition, in the above-described arteriosclerosis evaluating apparatus 10, the left-and-right-superior-limb blood-pressure ratio BBI is determined such that the lower one of the left and right systolic blood-pressure values $BPL_{SYS}$, $BPR_{SYS}$ is used as the numerator of the blood-pressure ratio BBI; and the higher one of the two systolic blood-pressure values $BPL_{SYS}$, $BPR_{SYS}$ is used as the denominator of the same BBI. However, a pre-selected one of the two sorts of systolic blood-pressure values $BPL_{SYS}$, $BPR_{SYS}$ may be used as the denominator of the blood-pressure ratio BBI. For example, in the case where each left-brachium systolic blood-pressure value $BPL_{SYS}$ is used as the denominator of blood-pressure ratio BBI, if the left superior-limb artery has stenosis and accordingly the left-brachium systolic blood pressure $BPL_{SYS}$ lowers, then the blood-pressure ratio BBI may be significantly greater than 1. Contrarily, if the right superior-limb artery has stenosis and accordingly the right-brachium systolic blood pressure $BPR_{SYS}$ lowers, then the blood-pressure ratio BBI may be significantly smaller than 1. Thus, the person can judge which one of the left and right superior limbs has arteriostenosis, depending on whether the blood-pressure ratio BBI is greater or smaller than 1.

In addition, in the above-described arteriosclerosis evaluating apparatus 10, the blood-pressure values are measured by the oscillometric method. However, blood-pressure values may be measured by so-called K-sound method in which blood-pressure values are determined based on respective values of cuff pressure at respective times when Korotkoff sounds are first and last detected. Otherwise, blood-pressure values may be measured by a supersonic Doppler method in which supersonic-wave oscillator and receiver, placed right above an artery, detect opening and closing of the arterial vessel during changing of cuff pressure.

Moreover, in the above-described arteriosclerosis evaluating apparatus 10, the CRT 68 is employed as the display device. However, a printer may be employed as the display device.

It is to be understood that the present invention may be embodied with other changes, improvements and modifications that may occur to a person skilled in the art without departing from the spirit and scope of the invention defined in the appended claims.

What is claimed is:

1. An arteriosclerosis evaluating apparatus, comprising:
   a left-superior-limb-blood-pressure measuring device which measures, with a cuff, a left-superior-limb blood pressure of a left superior limb of a living subject;
   a right-superior-limb-blood-pressure measuring device which measures, with a cuff, a right-superior-limb blood pressure of a right superior limb of the subject;
   a left-and-right-superior-limb-blood-pressure-ratio determining means for determining a left-and-right-superior-limb blood-pressure ratio as a ratio between the left-superior-limb blood pressure measured by the left-superior-limb-blood-pressure measuring device and the right-superior-limb blood pressure measured by the right-superior-limb-blood-pressure measuring device;
   a pulse-wave-propagation-velocity-related-information obtaining device which obtains at least one set of pulse-wave-propagation-velocity-related information that is related to at least one velocity at which at least one pulse wave propagates in at least one of (a) a first body portion of the subject that includes at least a portion of the left superior limb and (b) a second body portion of the subject that includes at least a portion of the right superior limb; and
   a display device which displays the left-and-right-superior-limb blood-pressure ratio determined by the left-and-right-superior-limb-blood-pressure-ratio determining means, and said at least one set of pulse-wave-propagation-velocity-related information obtained by the pulse-wave-propagation-velocity-related-information obtaining device, such that the left-and-right-superior-limb blood-pressure ratio and said at least one set of pulse-wave-propagation-velocity-related information are comparable with each other by a person.

2. An arteriosclerosis evaluating apparatus according to claim 1, wherein the pulse-wave-propagation-velocity-related-information obtaining device obtains said at least one set of pulse-wave-propagation-velocity-related information from said at least one of (a) said first body portion of the subject that includes at least said portion of the left superior limb and does not include the right superior limb and (b) said second body portion of the subject that includes at least said portion of the right superior limb and does not include the left superior limb.

3. An arteriosclerosis evaluating apparatus according to claim 2, wherein the pulse-wave-propagation-velocity-related-information obtaining device obtains said at least one set of pulse-wave-propagation-velocity-related information from said at least one of (a) said first body portion of the subject that includes at least said portion of the left superior limb where the left-superior-limb blood pressure is measured and (b) said second body portion of the subject that includes at least said portion of the right superior limb where the right-superior-limb blood pressure is measured.

4. An arteriosclerosis evaluating apparatus according to claim 1, wherein the pulse-wave-propagation-velocity-related-information obtaining device obtains a set of pulse-wave-propagation-velocity-related information from each one of (a) said first body portion of the subject that includes at least said portion of the left superior limb and does not include the right superior limb and (b) said second body portion of the subject that includes at least said portion of the right superior limb and does not include the left superior limb.

5. An arteriosclerosis evaluating apparatus according to claim 4, wherein the pulse-wave-propagation-velocity-related-information obtaining device obtains said set of pulse-wave-propagation-velocity-related information from said each one of (a) said first body portion of the subject that includes at least said portion of the left superior limb where the left-superior-limb blood pressure is measured and (b) said second body portion of the subject that includes at least said portion of the right superior limb where the right-superior-limb blood pressure is measured.

6. An arteriosclerosis evaluating apparatus according to claim 4, wherein the display device displays the left-and-right-superior-limb blood-pressure ratio, and the respective sets of pulse-wave-propagation-velocity-related information obtained from (a) said first body portion of the subject and (b) said second body portion of the subject, such that the left-and-right-superior-limb blood-pressure ratio and each of the respective sets of pulse-wave-propagation-velocity-related information are comparable with each other by the person.

7. An arteriosclerosis evaluating apparatus according to claim 6, wherein the display device further displays the left-superior-limb blood pressure measured by the left-superior-limb-blood-pressure measuring device, and the right-superior-limb blood pressure measured by the right-superior-limb-blood-pressure measuring device.

8. An arteriosclerosis evaluating apparatus, comprising:
   a left-superior-limb-blood-pressure measuring device which measures, with a cuff, a left-superior-limb blood pressure of a left superior limb of a living subject;
   a right-superior-limb-blood-pressure measuring device which measures, with a cuff, a right-superior-limb blood pressure of a right superior limb of the subject;
   a left-and-right-superior-limb-blood-pressure-ratio determining device which determines a left-and-right-superior-limb blood-pressure ratio as a ratio between the left-superior-limb blood pressure measured by the left-superior-limb-blood-pressure measuring device and the right-superior-limb blood pressure measured by the right-superior-limb-blood-pressure measuring device;
   a pulse-wave-propagation-velocity-related-information obtaining device which obtains at least one set of pulse-wave-propagation-velocity-related information that is related to at least one velocity at which at least one pulse wave propagates in at least one of (a) a first body portion of the subject that includes at least a portion of the left superior limb and (b) a second body portion of the subject that includes at least a portion of the right superior limb; and a display device which displays the left-and-right-superior-limb blood-pressure ratio determined by the left-and-right-superior-limb-blood-pressure-ratio determining device, and said at least one set of pulse-wave-propagation-velocity-related information obtained by the pulse-wave-propagation-velocity-related-information obtaining device, such that the left-and-right-superior-limb blood-pressure ratio and said at least one set of pulse-wave-propagation-velocity-related information are comparable with each other by a person.

\* \* \* \* \*